United States Patent [19]

Worrell et al.

[11] Patent Number: 4,786,374

[45] Date of Patent: * Nov. 22, 1988

[54] ELECTRO-CHEMICAL SENSORS AND METHODS FOR THEIR MANUFACTURE AND USE

[75] Inventors: Wayne L. Worrell, Narberth; Qing-Guo Liu, Pennsylvania, both of Pa.

[73] Assignee: University Patents, Inc., Westport, Conn.

[*] Notice: The portion of the term of this patent subsequent to Dec. 9, 2003 has been disclaimed.

[21] Appl. No.: 104,514

[22] Filed: Sep. 29, 1987

Related U.S. Application Data

[60] Continuation of Ser. No. 891,548, Jul. 29, 1986, abandoned, which is a division of Ser. No. 704,385, Feb. 22, 1985, Pat. No. 4,627,892.

[51] Int. Cl.$^4$ ............................................. G01N 27/58
[52] U.S. Cl. ................................... 204/1 T; 204/422; 264/570; 501/103; 501/152
[58] Field of Search ............... 204/422, 423, 421, 1 T; 501/103, 152; 264/570

[56] References Cited

U.S. PATENT DOCUMENTS

| | | | |
|---|---|---|---|
| 3,723,589 | 3/1973 | Kennedy | 204/421 X |
| 3,948,813 | 4/1976 | Holcombe et al. | 501/103 X |
| 4,266,979 | 5/1981 | Miyoshi et al. | 501/103 |
| 4,344,904 | 8/1982 | Yamada et al. | 501/103 X |
| 4,428,770 | 1/1984 | Worrell et al. | 204/422 X |

FOREIGN PATENT DOCUMENTS 1304291 1/1973 United Kingdom ................. 264/85

OTHER PUBLICATIONS

Dieter Janke, Solid State Ionics, ¾, pp. 599-604 (1981).
T. A. Ramanarayanan et al., J. Electrochem. Soc., pp. 1360-1363, Aug. 1979.
T. A. Ramanarayanan et al., J. Electrochem. Soc., pp. 1717-1721, Aug. 1980.
Wayne L. Worrell, Solid State Ionics ¾, pp. 559-563 (1981).
Wayne L. Worrell et al., IUPAC, pp. 503-509 (1969).
E. C. Subbarao, "Solid Electrolytes and Their Applications", pp. 261-294 (1980).
Wayne L. Worrell, Proc. Symposium on Metal-Slag-Gas Reactions & Processes", The Electrochem. Soc., pp. 822-833 (May 1975).
Wayne L. Worrell, Topics in Appl. Physics, vol. 21, pp. 143-168 (1977).
T. H. Etsell et al., "Electrochemical Oxygen Sensors-Analysis and Modifications", pp. 834-850.

Primary Examiner—G. L. Kaplan
Attorney, Agent, or Firm—Woodcock Washburn Kurtz Mackiewicz & Norris

[57] ABSTRACT

Improved electrochemical sensors are provided through isostatic processing techniques. Improved electrochemical sensors, especially those suitable for use in metallurgical melts, having, at once, long-term stability, improved sensitivity, and improved physical properties including thermal shock resistance are provided. In accordance with a preferred embodiment, unitary bodies comprising the sensing electrolyte and a source of reference potential are fabricated through isostatic processing techniques. Methods for the preparation of these improved sensors together with methods for the improvement of sensing, especially of oxygen in metallurgical melts are also disclosed.

35 Claims, 4 Drawing Sheets

ELECTRO-CHEMICAL SENSORS AND METHODS FOR THEIR MANUFACTURE AND USE

This is a continuation of Ser. No. 891,548 filed July 29, 1986, now abandoned, which in turn was a division of Ser. No. 704,385 filed Feb. 22, 1985 and now U.S. Pat. No. 4,627,892.

BACKGROUND OF THE INVENTION

This invention is directed to electrochemical sensors having improved sensitivity, stability and durability. This invention is also directed to processes for the fabrication of such sensors and to methods for their use. In accordance with preferred embodiments of the invention, improved sensors are provided for the detection of species such as oxygen, sulfur, carbon and the like in harsh environments such as at high temperatures in corrosive environments, and in metallurgical and other melts.

The detection of elemental and molecular species is an important aspect of numerous industrial and other procedures. For example, the detection of oxygen, sulfur, carbon and other species in metallurgical melts, in flue gasses, in chemical reactors and in other high temperature or corrosive situations is critical to the metals, utilities, chemicals, vitreous products and other industries. Moreover, caustic, corrosive, oxidative and other harsh conditions and environments strain the ability of sensor manufacturers to prepare electrochemical sensing devices capable of surviving such conditions and environments while retaining the ability to perform the desired sensing duties in an accurate and reliable fashion and for reasonable periods of time.

One area presenting particularly stingent requirements for sensing devices is the field of metals purification and processing. It is commonly necessary to measure the oxygen, sulfur, carbon and other contents of molten metals such as iron and steel. To do so, it is known to immerse electro-chemical sensors in such melts. The electromotive force, EMF, generated by the sensor is then monitored and related to the activity or concentration of the atomic or molecular species of interest. Heretofore, electrochemical sensors for the testing of such melts have demonstrated severe shortcomings including short operating lifetimes (often only a few minutes), high failure rates, poor reproduceability, low sensitivity and other faults.

General considerations for the development of electro-chemical sensors, especially those useful in metallurgical melts, are discussed in Worrell, "Developing New Electrochemical Sensors", *Proceedings of the Symposium on Metal-Slag-Gas Reactions and Processes,* Electrochemical Society, Princeton, N.J., (May 1975), incorporated herein by reference. Thus, it has long been desired to provide electrochemical sensors, especially those suited for harsh environments, which exhibit improved sensitivity, long-term physical and electrochemical stability, and physical durability.

It has also long been desired to provide methods for the preparation of electrochemical sensors which are, at once, effective in obtaining improved sensor qualities while securing reduced manufacturing costs. Methods of sensing and measurement which provide more accurate, longer term, and more sensitive information have also been sought. Prior to the present invention, however, these long felt needs have not been satisfied. Improvements attempted by others have failed to attain the desired goals.

Electrochemical sensors adapted for the measurement of oxygen in liquids such as in metallurgical metals are known. See in this regard "Developing New Electrochemical Sensors", Worrell, supra; "Oxide Solid Electrolytes", Worrell, *Topics in Applied Physics,* Geller Ed., Springer (1977); and "The Measurement of Oxygen Chemical Potentials for the Calcium Fluoride Solid Electrolyte", Worrell et al., *Journal of the Electrochemical Society,* Vol. 126, No. 8, pp. 1360–1363 (1979). The foregoing references are incorporated herein by reference in order to describe more fully the electrochemical determination of elemental compositions employing solid electrolyte sensors. The foregoing publications disclose the employment of certain simple solid solutions such as those of zirconium oxide and thorium oxide in the electrochemical detection of oxygen.

Electrolytes suitable for the electrochemical measurement of sulfur or carbon under laboratory conditions have been disclosed. Calcium fluoride, for example, has been proposed for such use. See "The Measurement of Sulfur Chemical Potential Differences Using a Calcium Fluoride Solid Electrolyte," Worrell et al., *Journal of the Electrochemical Society: Electrochemical Science and Technology,* pp. 1717–1721, August 1980; and "Galvanic-Cell Investigation With a $CaF_2$ Solid Electrolyte at Elevated Temperatures," Worrell, *Solid State Ionics* ¾, pp. 559–563 (1981). Further attempts at the electrochemical measurement of sulfur have been reported. Thus, the employment of calcium sulfide-based electrolytes is reported in "Development of the High-Temperature Technology, IUPAC, pp. 503–509 (1969). In U.S. Pat. No. 4,428,770, in the names of the present inventors, novel sulfur and carbon sensors for metallurgical applications are disclosed. That patent together with each of the foregoing references are incorporated herein by reference. Other systems for measuring sulfur and carbon potentials are discussed in that patent.

For many years, oxygen sensors for metallurgical melts have been constructed from zirconia, $ZrO_2$, partially stabilized with aliovalent materials such as calcium oxide, $CaO_2$ or magnesia, $MgO_2$. Thus, in one type of sensor a calcium oxide-stablized zirconia solid electrolyte pellet was welded into a quartz tube for insertion into melts. The tube was either open to a gas (such as the atmosphere) to provide a source of reference potential, or was provided with a solid reference electrode material such as metal-metal oxide mixture. EMF measurement and thermocouple means were also typically provided as appropriate. Such electrochemical sensors, while capable of some uses in metal melts, suffered from a lack of physical integrity leading to unreliable data, lack of reproducability, and failure after short periods of time when placed into metallurgical service.

In the 1970's efforts were made to develop improved solid electrolyte-based sensors, especially oxygen sensors, for metal melts. In this regard, it was hoped to overcome the physical instability and tendency toward thermal fracture of previous sensors through stabilization of the electrochemical material and improved physical processing methods for the sensor fabrication. The quartz tube was discarded and a tube formed from the electrolyte material itself employed. Partially stabilized zirconia, $ZrO_2$ with about 3 wt % of MgO was blended together, formed into a tubular shape, compacted, and densified through sintering. The resulting, sintered electrolyte material comprises two phases, cubic and tetragonal, and exhibits improved mechanical strengths and resistance to thermal shock. The tube can be filled with a solid reference electrode material together with thermocouple and electrical lead means as desired.

The tube comprising a two-phased electrolyte can be used as an oxygen sensor in metallurgical melts and is widely used for this purpose today. While exhibiting utility for this purpose, the foregoing two-phase electrolyte tube devices still suffer from severe shortcomings. Such devices are extremely short-lived, being capable of use on the order of only a few minutes. While after special modification some tubes can last for as long as ten minutes before usefulness is lost, such lifetime is far less than is desired and the resulting data is of poor quality. Since the partially stabilized electrolyte in a two-phased mixture has, overall, an undesirably high electronic contribution to the conductivity, the device is incapable of accurately sensing oxygen concentrations below about 10 parts per million. Moreover, the electromotive force developed by such cells decreases substantially with time due to a progressive short-circuit of the cell. At the same time, such tubes are relatively expensive to manufacture.

The newest type of oxygen sensor proposed for use in metallurgical melts is the "needle sensor". See, in this regard, Janke, *Solid State Ionics*, Vol. ¾, pp. 599–604 (1981). This sensing device is fabricated through an expensive sputtering technique whereby a molybdenum wire is typically coated with sputtered chromium-chromium oxide and then overcoated with sputtered stabilized zirconia. In has been found that such sensors are incapable of measuring low oxygen concentrations (less than about 20 ppm).

In the preparation of sensors such as oxygen sensors, which employ solid state electrolytes, it is known to be desirable to maximize the ionic conductivity of the electrolyte material and to minimize the electrical conductivity thereof. Sensing electrolytes having substantial electronic conductivity exhibit unstable results at low concentrations of oxygen when the electronic conductivity increases. It is also desired to maximize the intimacy of contact between the electrode material and that of the reference electrode material so as to minimize the equilibration time at the interface between the two materials. Of course, all of this must be obtained while maintaining acceptable physical integrity, mechanical strength and thermal shock resistance in the whole of the sensor.

The sensors in accordance with this invention solve the needs which exist for improved sensing devices and successfully address the requirements for improved sensors without suffering from the shortcomings exhibited by previous sensors.

OBJECTS OF THE INVENTION

It is a principal object of this invention to provide electrochemical sensors, especially those for harsh environments, having improved electrochemical and physical properties.

It is another object of this invention to provide processes for the preparation of improved electrochemical sensors.

Yet another object is to provide improved methods for measuring the activity or concentration of an atomic or molecular species, especially under harsh conditions or at high temperatures.

Yet another object is to fabricate solid state sensors having improved sensitivity, greater stability, and improved physical properties including resistance to thermal shock.

A further object is to provide improved electrochemical sensors at reduced costs while obtaining improved performance and physical properties.

A still further object is to secure the improved processing of metals through longer-term, more accurate and more sensitive monitoring of the content of metallurgical melts.

Yet another object is to provide electrochemical sensors without the employment of sintering, sputtering or other high temperature densification techniques.

These and other objects will become apparent from a review of the instant specification.

SUMMARY OF THE INVENTION

In accordance with this invention, electrochemical sensors for atomic or molecular species are constructed comprising a shaped body isostatically formed from a blend. The blend comprises an ionically conductive solid solution electrochemically sensitive to the species to be detected having a fluorite crystal structure. Such material comprises a metal oxide, preferably one having a fluorite crystal structure and, admixed with the metal oxide, an oxide of an element from group IIA or IIB of the periodic table in an amount sufficient to render the blend ionically conductive. Following the isostatic formation of the shaped body, the body is not densified through thermal means. In accordance with certain preferred embodiments, a reference electrode composition is also provided in physical contact with the shaped body. It is preferred that the reference electrode also comprise an isostatically compressed form and that the compressed form be contained within the shaped body formed from the blend. Accordingly, it is preferred to provide unitary or combination sensors having both sensing and reference electrode components.

It is also preferred that the blend be pre-processed prior to the final isostatic formation of the shaped body. Accordingly, the blend is isostatically compressed at a pressure of at least about 35,000 psi in accordance with these preferred embodiments, and the resulting compressed structure comminuted prior to the final isostatic formation of the shaped body. The isostatic formation of the shaped body is preferably performed at a pressure of at least 70,000 psi, but is not thermally densified. It is preferred that the shaped body have a density less than about 90% of the theoretical density and that the same comprse at least about 95% of a single solid phase.

For sensing methods in metallurgical melts and in other harsh environments, especially applications directed to the sensing of oxygen, it is preferred to employ zirconium oxide as the metal oxide since that material has good electrochemical properties towards oxygen. The admixed oxide for the zirconium oxide or other metal oxide in accordance with these embodiments preferably comprises an oxide of a metal selected from groups IIA or IIIB of the periodic table, especially from the group consisting of scandium, yttrium, calcium and magnesium. These are present in the metal oxide compositions to form the fluoride crystal structure solid solution of the blend in amounts up to about 30% in accordance with preferred compositions.

The reference electrodes which are preferably used in conjunction with the shaped body of the instant invention may comprise a wide range of materials known for this use but preferably comprise a metal together with one of its oxides, especially of chromium or molybdenum.

Sensors in accordance with the instant invention are capable of longer term use than their predecessors. Since such use is accompanied by unparalleled stability and sensitivity, it is now possible to monitor the condition of harsh environments such as metallurical melts over long periods of time and with improved degrees of sensitivity and accuracy. Accordingly, improved methods for the preparation of metals metallic alloys and the like employing these sensors are now possible.

DETAILED DESCRIPTION OF THE PREFERRED EMBODIMENTS

Figure 1A:
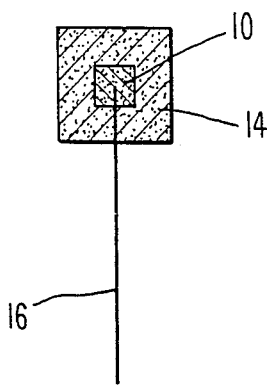
FIGS. 1A and 1B depict sensors in accordance with certain embodiments of the instant invention.

It has now been found that electrochemical sensors can be formed through isostatic compression techniques which have excellent thermal shock resistance, high ionic conductivity, low electronic conductivity and good sensitivity together with long germ electrochemical stability and physical durability. For the first time, it is now possible to prepare electrochemical sensors such as oxygen sensors for metallurgical melts, which are, at once, stable and sensitive and which can be used for long periods of time and reused if desired. Unlike devices proposed by prior practitioners who strove for maximum densification of electrochemical sensing materials for use in melt, through sintering, plasma processing, sputtering and the like, it has now been found that comparatively less dense sensing materials can be formed which are ideally suited for sensor use. Accordingly, sensors are formed without thermal densification techniques.

It was previously believed that electrochemical sensors for high temperature use such as in metallurgical melts should have maximum density. This was believed to be necessary in order to prevent the migration of materials into the sensing body and to avoid the concomitant shorting out of the sensor. To this end, prior workers in the field used high temperature processing for the preparation of such electrochemical sensors. Thus, such materials have generally been either sintered or formed through plasma techniques or sputtering. The foregoing high temperature processing required modification of the sensing material in order to comport with the need for thermal shock resistance in such sensors, however.

Such modifications, in the reduction in materials added to create or enhance ionic conductivity and in the adoption of two-phased systems, have tended deleteriously to affect the electrical properties of the sensors by lowering deleteriously the ratio of ionic to electronic conductivity in them. Partial stabilization of zirconia for oxygen sensors for use in metallurgical melts with magnesium oxide as has been commonly practiced permits an oxygen sensor to be formed having certain utility. The compositions which are employed, however, have substantial electronic conductivities, such that low oxygen concentrations, i.e. those less than about 10 ppm, cannot be accurately detected. At the same time, the overall useful lifetime of the sensors thus formed is remarkably short, on the order of a few minutes and no more than about 10 minutes with specially modified apparatus.

In direct contradistinction to the approaches taken by prior practitioners in this field, the instant invention does not employ sintering, plasma processing, sputtering or similar high temperature densifying techniques for sensor formation. Rather, sensors in accordance with the instant invention are prepared through isostatic compression techniques without thermal densification. Unlike prior materials which relied upon dense and two-phased materials for improvement in thermal shock resistance which led to deleterious effects upon the electrochemical properties of the resulting sensors, sensors in accordance with the present invention can maximize the electrochemical properties of the devices. This has now become possible through the surprising discovery that shaped bodies of electrochemically sensitive materials can be formed through isostatic processing techniques which are not liable to invasion by foreign materials with subsequent destruction of the sensor through "shorting out" or otherwise.

Accordingly, electrochemical sensors having electrochemically sensitive portions with densities less than 90%, preferably below about 80%, and even as low as 60–70% of the theoretical density of the sensing material, have been formed hereby. These less dense materials have excellent thermal shock resistance and do not require two phases for stability. This new freedom to concentrate upon the maximization of electrochemical properties of sensors in accordance with the present invention permits the fabrication of a class of such sensors having unprecedented sensitivity at low oxygen concentrations and long term stability with excellent physical durability, thermal shock resistance, and long term utility.

The sensors which are objects of the present invention are solid state electrochemical sensors for atomic and molecular species. Thus, members of the family of sensing devices which exist in the solid state and which are capable of generating an electromotive force, EMF, upon contacting the atomic or molecular species to be sensed, are objects of this invention. The present improvements were developed especially for use in the extraordinarily harsh conditions which attend metallurgical purification and processing in metallurgical melts. Exemplary of these is the processing of iron and steel. Thus, the sensors and methods in accordance with this invention are particularly suitable to the determination of oxygen and, it is believed, carbon, sulfur and other species in metallurgical melts.

It is believed that the instant sensors and the related methods may also find utility in environments other than metallurgical melts such as high temperature reaction vessels or atmospheres, flue gasses, power boilers, pollution control equipment, and a whole host of oxidative, corrosive, high temperature, and other harsh environments. It is also anticipated that sensing devices in accordance with this invention will also find utility in less harsh environments as well.

It is believed that sensors in accordance with the instant invention can be fabricated which may be sensitive to a wide range of materials including oxygen, carbon, sulfur, acidic gasses such as sulfur dioxide and sulfur trioxide, oxides of nitrogen, and many other species.

For the detection of sulfur or carbon, it is preferred to employ compositions similar to those disclosed in U.S. Pat. No. 4,428,770, incorporated herein by reference. Thus, a carbide or sulfide of an element of group IIA or IIIB of the periodic table is preferably also included. A carbide or sulfide from group IVB may also be used such as those of titanium, zirconium or hafnium.

Sensors in accordance with this invention comprise ionically conductive materials which are sensitive to the species to be detected. In this regard, those of ordinary skill in the art appreciate that electrochemical sensors are desired to have the greatest possible ionic conductivity while, at the same time, having the smallest possible electronic conductivity. Sensing devices having relatively large ionic conductivities coupled with relatively small electronic conductivities are able to demonstrate relatively high reliability and reproducibility in detecting the activity or concentration of the species. It is necessary to select ionically conducting materials which are suitable for the detection of the species to be detected. In most cases, such conducting materials will comprise blends comprising or preferably consisting of solid solutions having fluorite lattice structure.

For detection of oxygen in metallurgical melts, it is preferred to employ metal oxides having a fluorite crystal structure or capable of having solid solutions with such structures such as zirconia, hafnia, thoria, ceria and lanthania. It is preferred to employ materials based upon zirconium oxide since that material is known to generate adequate EMF's in metallurgical melts and to be generally suitable as a base material for sensing devices for such employment. Mixtures may also be useful.

It is also generally understood that the metal oxides which are sensitive to the species to be sensed, i.e., which generates an EMF when in contact with such species, is seldom able to be fabricated into suitable electrochemical sensors without modification into a blend to improve the ionic conductivity. Accordingly, an oxide from group IIA or IIIB of the periodic table is preferably blended with the metal oxide through admixture in proportions sufficient to render the resulting blend ionically conductive to a degree sufficient for sensing. Such oxides for admixture may comprise calcium, magnesium, strontium, barium, scandium, yttrium and lanthanum oxides and mixtures thereof. It is greatly preferred that the admixed oxide be included in the blends with metal oxide in proportions which permit the blends to comprise solid solutions which retain fluroite crystal structures. In this regard, proportions which are consistent with this goal may be determined in accordance with the procedures of "Oxide Solid Electrolytes", Worrell, *Topics in Applied Physics*, Vol. 21, p. 143 et seq., Springer (1977), which in incorporated herein by reference. In the case of zirconium oxide sensors designed for use in metallurgical melts for the detection of oxygen, it is preferred to employ metal oxides such as calcium, magnesium, yttrium, or scandium oxide for this purpose. Yttria and calcium oxide are most preferred. Additional aliovalent materials may be useful for modification of the preferred zirconium oxide materials. Those of ordinary skill in the art will understand that routine experimentation may be necessary in order to identify preferred aliovalent compositions for particular sensing systems in accordance with these embodiments.

Admixed oxide is blended with the metal oxides in an amount sufficient to improve the ionic conductivity and, preferably, also the physical stability of the resulting sensors formed therefrom. Thus, the metal oxide and admixed oxide are blended to form a blend which is useful in the subsequent formation of the electrochemical sensors of the invention. While admixed oxide is included in an amount sufficient to improve ionic conductivity of the resulting blend, in general, amounts of admixed oxide up to about 30% and preferably between about 2 and 25% and more preferably between about 3 to 15% by weight are preferred for most zirconium oxide systems.

The foregoing blend is preferably provided in particle sizes and forms which are maximally suited for the practice of this invention. Thus, it is preferred to employ aggregates of smaller particles of blend yielding average aggregate sizes between about 100 and 500 microns in the blend. For zirconium oxide oxygen sensing systems, it is preferred to employ aggregate sizes between about 150 and about 425 microns. Other systems may beneficially employ differing particle size ranges, however.

The foregoing aggregate sizes are preferably achieved by isostatic compression of the blend. Thus, the blend is preferably isostatically compressed at a pressure in excess of about 30,000 psi to form a compressed shape which is subsequently comminuted in a conventional crushing process to yield the desired aggregate sizes. For zirconium oxide oxygen sensors, it is preferred to undertake this pressing using pressure of about 50,000 psi. The blends (as opposed to the isostatically-formed shaped bodies) are preferably sintered prior to aggregation through isostatic compression. Such materials are commercially available preblended and sintered.

Following the comminution of the pre-compressed shape, the crushed aggregate is subjected to a second isostatic compression. Thus, the same is formed into a shaped body under isostatic pressure preferably in excess of about 70,000 psi. For zirconium oxide oxygen sensors, isostatic compression to form the shaped body preferably takes place at pressures in excess of about 75,000 and even more preferably in excess of about 80,000 psi. Compression is maintained for a period of time sufficient to form the shaped body and to cause the same substantially to coalesce. A few minutes is generally sufficient for this purpose.

Isostatic compression can be achieved in a number of ways. Generally, an amount of the blend is encapsulated by a physically deformable matrix, such as a matrix of rubber, and caused to be subjected to pressure. By virtue of the deformability of the deformable composition or rubber, substantially identical pressures are exerted on all portions of the compressed blend. The blend may be isostatically compressed into any number of shapes to form the shaped body of the invention. While it is convenient to provide generally rectalinear shapes, free-form, ovoid, cylindrical, and other shapes may also be employed.

The resulting shaped body, when fitted with appropriate sources of reference potential and EMF measuring means, is capable of detecting the presence of species such as oxygen in metallurgical melts. As will be explained more fully hereinafter, the shaped body is preferably elaborated into a more complex device in order to facilitate sensing procedures.

The structure of the shaped body following isostatic processing is significant. Thus, unlike prior attempts of preparation of sensors for metallurgical and other applications, it has not been attempted to render the sensing bodies maximally dense. Thermal densification techniques such as sintering, plasma processing or sputtering are avoided. Contrary to the prevailing view of those of ordinary skill in the art that lesser densities in such sensors would render the same liable to incursion of electronically conducting materials, which would render the same liable to electrical shorting, or to gas penetration, it has now been found that sensors having densities substantially less than the maximum theoretical value are highly utile. Accordingly, the present sensors have preferred densities less than about 90% of the theoretically maximal density of the blend materials. It is even more preferred that lesser densities be employed. Thus, densities less than about 80% and even more preferably less than about 70% of the maximum theoretical density are employed. For zirconium oxide-based metallurgical oxygen sensors, densities between 60% and about 70% of the theoretical maximum densities are preferred.

Such shaped bodies also preferably are comprised of a single solid phase rather than two or more phases. Accordingly such bodies preferably have more than about 95% and even more preferably, more than about 99% of a single phase.

In accordance with preferred embodiments of the invention, the isostatically-formed, shaped bodies are provided with a source of reference potential in physical contact therewith. As will be appreciated by those of ordinary skill in the art, numerous sources of reference potential for solid state electrochemical sensing devices are known. Such persons will have no difficulty in identifying suitable materials for use as a source of reference potential. While it is also possible to use gaseous or liquid means for the attainment of reference potential, solid state sources are much preferred.

It is generally preferred to employ compositions comprising mixtures of a metal and a metal oxide for use as a source of reference potential in conjunction with zirconium oxide metallurgical oxygen sensors. Numerous metal-metal oxide combinations may be employed for this purpose including preferred blends upon chromium and molybdenum. For zirconium oxide based metallurgical oxygen sensors, reference electrodes comprising chromium-chromium oxide, or molybdenum-molybdenum oxide are preferred.

The shaped body comprising the isostatically formed sensing blend in accordance with this invention and the source of reference potential may be arrayed in a wide variety of forms and formats in accordance with the spirit of the invention. Thus, the same may be included in a quartz or other suitable container or tube and fitted with suitable thermocouple, contact and potential measuring means as desired and appropriate. In accordance with the practice of a preferred embodiment of the invention, however, particularized structures have been found to be exceptionally practical, useful and economical for preparing electrochemical sensors having internal sources of reference potential. Thus, it is preferred to prepare an isostatically compressed or otherwise fabricated form comprising the reference electrode material such as metal and metal oxide, to cause the same to be surrounded by the blend comprising ionically conductive sensitive materials and aliovalent stabilizing compositions, and to affect isostatic compression of the blend as described hereinbefore to form the shaped body. The resulting unitary structure will comprise the source of reference potential, preferably in an isostatically compressed form, substantially contained within the isostatically compressed, shaped body. Of course, potential measuring means, thermocouple means and other desired additional components of electrochemical sensors will preferably be provided for as well.

Certain preferred embodiments will be discussed in accordance with the following examples. These examples are intended to be illustrative only and are not to be construed as limiting.

EXAMPLE 1

Electrolyte blends for formation of shaped bodies are prepared from yttria-stabilized and calcium oxide-stabilized zirconia powders. Thus, 99.9% pure zirconia powder is admixed with approximately 12 mole percent of $Y_2O_3$ or approximately 15 mole percent CaO for use as electrolyte materials. Other compositions such as 6-15 mole percent yttria-zirconium oxide and 7-16 mole percent calcium oxide-zirconium oxide are also suitable for such electrolytes. The average particle sizes for the foregoing materials are maintained within the range of about 0.5 to about 5 microns and preferably within the range of 0.8 to about 1.5 microns. The zirconia-yttria or zirconia-calcium oxide blend is then pre-pressed in a rubber mold at 50,000 psi using an isostatic press. The pre-pressed block is then crushed to −50 mesh powder (less than about 300 microns) and this coarse powder used to prepare shaped bodies.

EXAMPLE 2

Preferred reference electrode sources are prepared from blends of molybdenum and molybdenum oxide or chromium and chromium oxide having purities of about 99.9%. If molybdenum and molybdenum oxide are used, their particle sizes are approximately −325 mesh (less than about 44 microns). If chromium and chromium oxide are used, they are conveniently present in particle sizes of about 2 microns and 5 microns respectively. The foregoing materials are available from the Alfa Company.

EXAMPLE 3

A shaped form of reference material was formed through an isostatic pressing method. Thus, the chromium-chromium oxide or molybdenum-molybdenum oxide reference powder mixtures comprising from about 2 to about 20% oxide by weight were mixed with up to about 15 wt % of ammonium carbonate and then placed into a rubber mold. Molybdenum wire from 0.2 to about 1.0 millimeters in diameter was embedded into the reference powder to serve as an electric lead. An isostatic press was then used to compress the reference electrode material into a pellet at approximately 60,000 psi. A reference electrode pellet of about 3-5 millimeters in diameter and 5-7 millimeters high was formed. The compressed pellet was dried at about 100° C. to evaporate the ammonium carbonate.

EXAMPLE 4

Another method of forming a reference electrode comprised mixing the chromium-chromium oxide or molybdenum-molybdenum oxide reference powders together with glycerol to form a paste. The paste was then placed on a spring coil formed from molybdenum wire 0.25-0.50 millimeters in diameter and the resulting reference electrode pellets dried for about one day in air and one day at 100° C. Following additional drying in a vacuum of about 0.01 Torr at 130° C. for day, a reference electrode pellet of about 2-3 millimeters in diameter was secured. This method of preparing reference electrode pellets is somewhat less desirable than the isostatic reference electrode pellet preparation method. It is suitable for use in sensors wherein slightly less rigorous performance characteristics can be tolerated, however.

EXAMPLE 5

A reference electrode pellet in accordance with either of Examples 3 or 4 was placed into a rubber mold and surrounded by the pre-pressed, comminuted electrolyte powder of Example 1. Isostatic compression at about 85,000 psi formed a shaped body from the electrolyte blend substantially completely surrounding the reference electrode pellet. It is convenient to prepare sensors in accordance with this technique having diameters from about 4-10 millimeters and lengths of about 8-12 millimeters. When employing the paste-formed reference electrode for less rigorous applications, somewhat smaller overall sensor sizes can preferably be prepared. Thus, such sensors having diameters of from about 3-5 millimeters with lengths of from about 2-5 millimeters are conveniently fabricated.

Figure 1B:
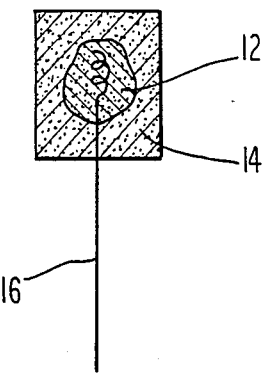

FIGS. 1A and 1B depict oxygen sensors in accordance with the foregoing examples. Thus, either isostatically formed reference electrode 10, or paste-formed reference electrode, 12 is preferably substantially completely surrounded by isostatically formed shaped body 14 comprising the sensing electrode material. Potential transmission means 16 such as molybdenum wire are also provided.

EXAMPLE 6

Another technique for the preparation of oxygen sensors in accordance with the invention provided a molybdenum wire of diameter 0.5 millimeters wound into a spring coil of about 1.5 millimeters in diameter and 7-10 millimeters in length with an associated straight lead 20 millimeters in length. The coiled portion of the wire was inserted into a reference electrode paste comprising reference powder admixed with anhydrous alcohol and glycerol. Dipping into the paste several times provided a globular coating of reference paste about the spring-form portion of the wire. After air drying for one day at about 100° C., the globular structure with attendant molybdenum lead was inserted into an electrolyte paste comprising yttria-stabilized zirconia admixed with anhydrous alcohol and glycerol. Collection of a substantially continuous coating of electrolyte was accomplished. The cell was then dried in air for about one day at 100° C. and in vacuum at about 130° C. for an additional day. The assemblage was then inserted into a rubber solution for forming a rubber layer thereupon or caused to be wrapped in a thin rubber film. The assemblage was then isostatically pressed at about 85,000 psi in an isostatic press to provide a compact oxygen sensor.

Each of the foregoing examples 5 and 6 provides unitary sensors having both reference and test electrode formations.

EXAMPLE 7

Oxygen sensors in accordance with the foregoing examples were preferably mounted on a quartz or porous alumina tube employing a high temperature stable alumina cement. For longterm oxygen sensors, chromium (if a chromium-chromium oxide reference electrode material is selected) or molybdenum (when a molybdenum-molybdenum oxide reference electrode material is selected) was loaded into the porous alumina or quartz tube to absorb any residual oxygen which may be found in the cell. After drying at 100° C. for about 1 day, the integrated sensor was tested in a laboratory furnace formed of molybdenum silicide heating elements.

Commercial pig iron or pure iron was used for testing. The metal was put into an alumina (or graphite for pig iron) crucible about 30 millimeters in diameter and 60 millimeters high. The iron was melted in a purified argon atmosphere. At a temperature of about 1600° C., the oxygen sensor combined with an alumina tube was inserted into the molten melt for testing. The electromotive force generated by the interaction of the sensor with the melt was measured by a Keithley 177 microvolt DMN meter interfaced with a data collection computer. For long term oxygen sensing tests. the electromotive force was read every minute. For tests of expendable oxygen sensors the electromotive force was read every second.

Commercially-available oxygen sensors employing chromium-chromium oxide reference electrodes supplied by the Electro-Nite Company were also tested for comparison purposes. When employing a chromium-chromium oxide reference electrode, the reference electrode lead was connected to the negative pole of the volt meter. The reference electrode lead was connected to the positive pole of the volt meter for oxygen sensors employing molybdenum-molybdenum oxide reference electrodes.

Figure 2A:
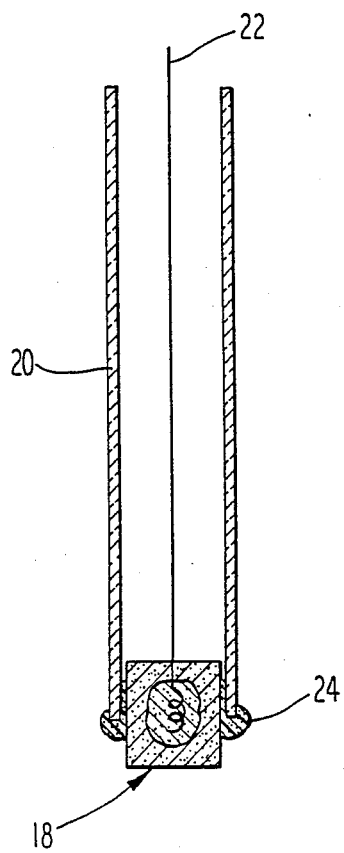
FIGS. 2A and 2B are schematic drawings of certain preferred sensors in accordance with this invention which are especially suited for use in metallurgical melts.

In FIG. 2A, an oxygen sensor in accordance with one of the foregoig examples, 18 is cemented to a quartz tube, 20 through the intermediation of high temperature alumina cement, 24 or similar material. Electrical lead 22 such as a molybdenum wire, is also provided.

Figure 2B:
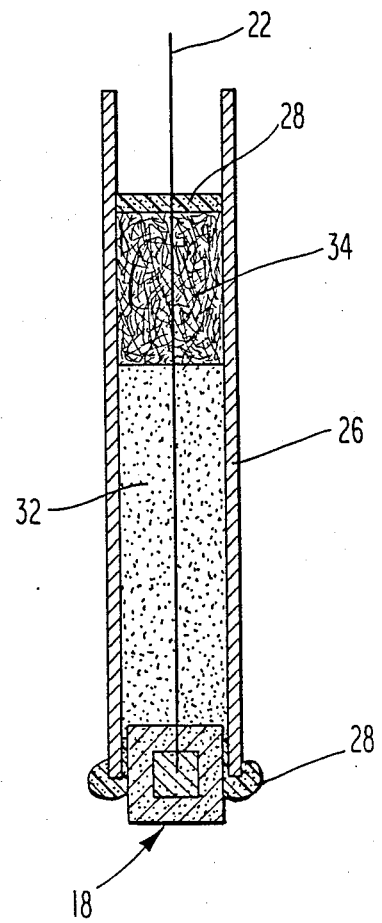
Figure 3:
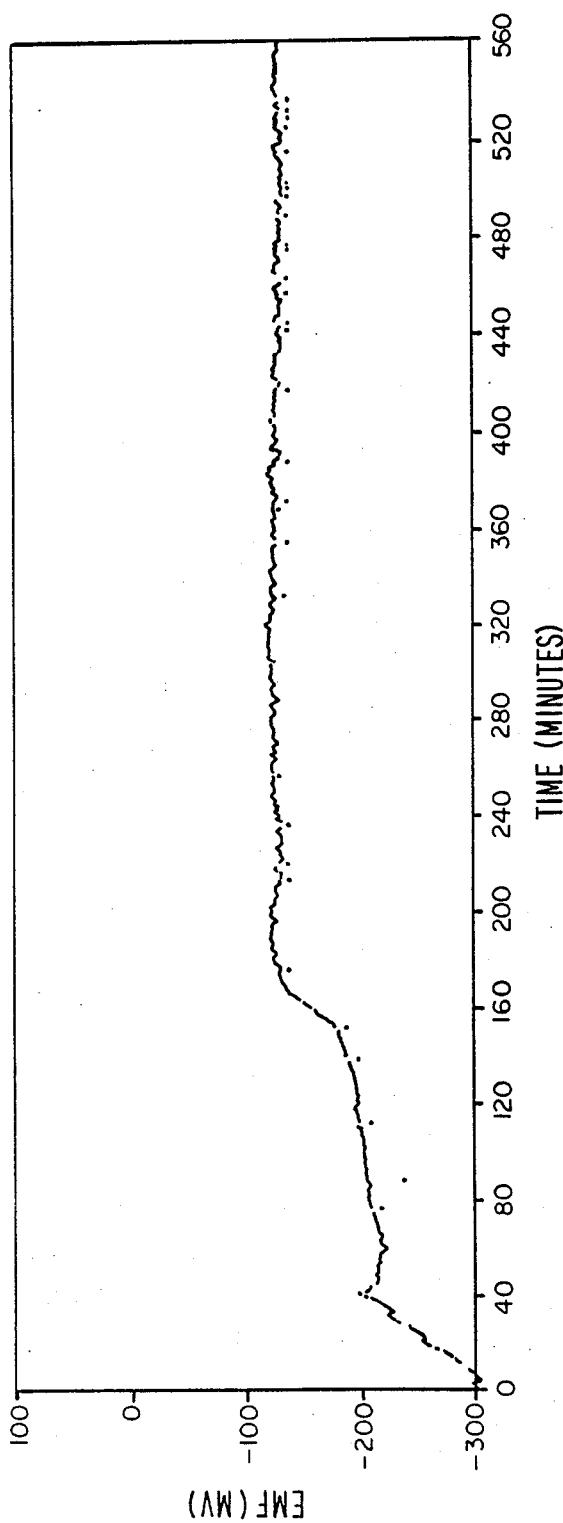
FIGS. 3, 4 and 5 depict performace of oxygen sensors for metallurgical melts in accordance with certain preferred embodiments of the instant invention.

In FIG. 2B, an oxygen sensor in accordance with one of the foregoing examples, 18 is adhered to an alumina tube 26 with high temperature cement such as alumina cement 28 in such a fashion as to form a cavity. The cavity is filled with molybdenum powder, 32 when a molybdenum-molybdenum oxide reference electrode is selected together with silica fiber, 34. A molybdenum wire lead, 22 is also provided.

An oxygen sensor in accordance with the foregoing Example 5 employing isostatically compressed chromium-chromium oxide reference electrode material (20% chromium oxide) was tested in pig iron melted in a graphite crucible under an argon atmosphere at 1600° C. The graphite crucible served as the second electrical lead for potential measurement. Initial oxygen concentration was extremely low, less than about 0.6 parts per million, resulting in an EMF of about −300 millivolts. To increase the oxygen concentration, a quartz tube was used to bubble air into the melt for several minutes while a hole on the cover of the vessel was opened to provide for circulation. EMF decreased with increasing oxygen concentration. When the testing had lasted for three hours, the hole in the reaction vessel cover was closed and air bubbling terminated. The EMF stabilized at a constant −120 to −130 millivolts corresponding to 5.4 ppm oxygen. The oxygen sensor demonstrated essentially constant EMF readings from the termination of oxygen bubbling at about 180 minutes until termination of the experiment at 560 minutes. At the conclusion of the experiment, the oxygen concentration was verified by two cells from commercial oxygen sensors (Celox ®) supplied by the Electro-Nite Company. These sensors gave the same EMF as that given by the foregoing oxygen sensor within experimental limits.

Figure 4:
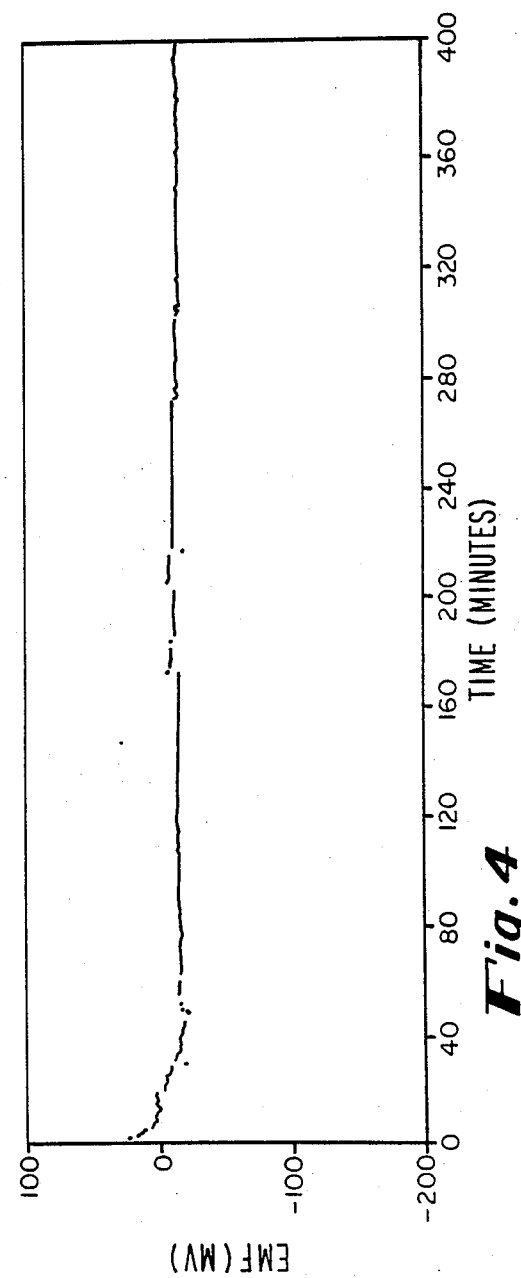
Figure 5:
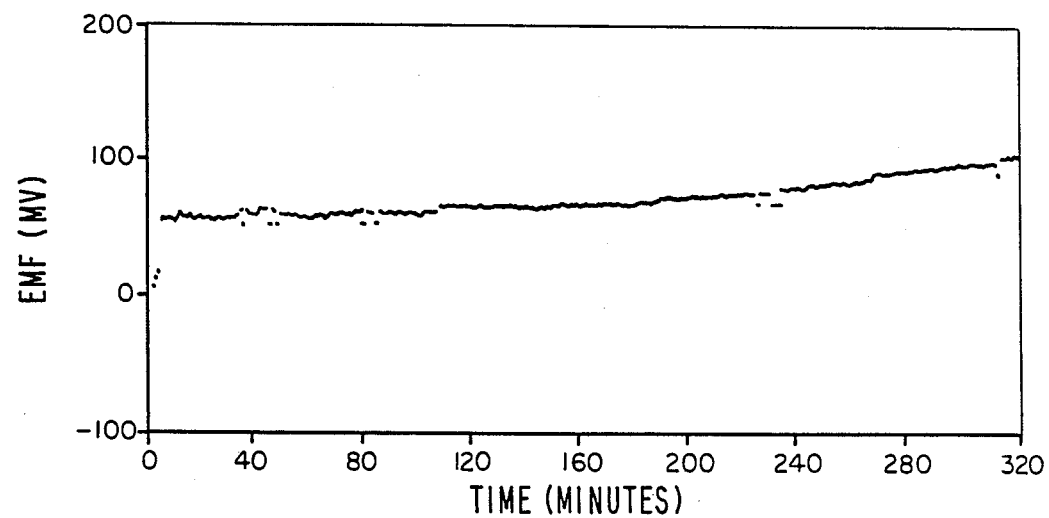

Similar long term oxygen sensors were tested at higher oxygen concentrations by submerging them in pure iron melted in an alumina crucible under an argon atmosphere. Carbon was used to change the oxygen concentration in the melt. A molybdenum wire embedded in an alumina tube was inserted into the melt as the second electric lead. The oxygen sensor was tested and survived in excess of 5 hours at these higher oxygen concentrations. FIGS. 4 and 5 demonstrate the stability of the sensors at oxygen concentrations corresponding to 21 and 60–77 ppm of oxygen respectively.

Similar sensors employing molybdenum-molybdenum oxide (20 wt % oxide) reference electrode mixtures are suitable as long-term oxygen sensors in metallurgical melts. It has been found that such sensors can last over 5 hours in ferrous melts having oxygen concentration above about 100 ppm. The same sensors have lasted from 1 to 2 hours when the oxygen concentration at such melts is only a few ppm due to considerable short circuit current evidenced under those conditions, however. It is anticipated that molybdenum-molybdenum oxide reference electrode-based sensors will be preferable for the measurement of high oxygen concentrations and that chromium based reference electrode systems will be preferable for lower oxygen concentrations.

Figure 6:
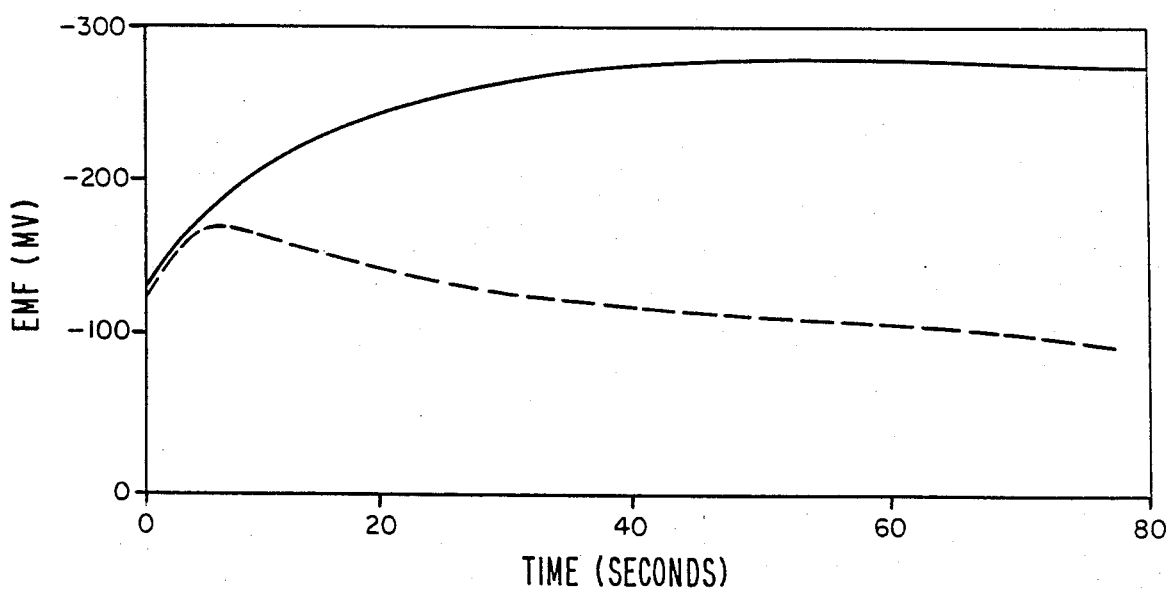
FIGS. 6, 7 and 8 compare the performance of certain oxygen sensors for metallurgical melts in accordance with this invention with prior commercial oxygen sensors for such uses.
Figure 7:
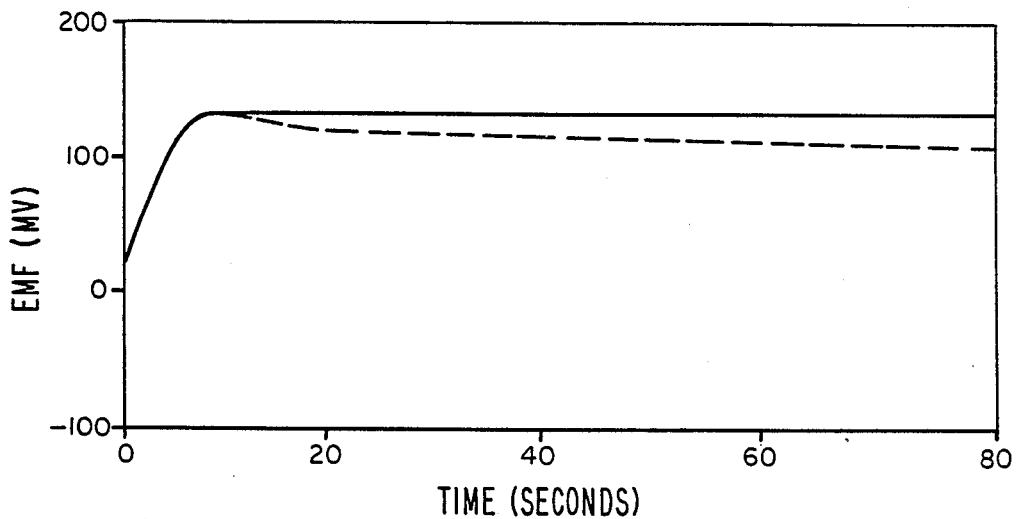
Figure 8:
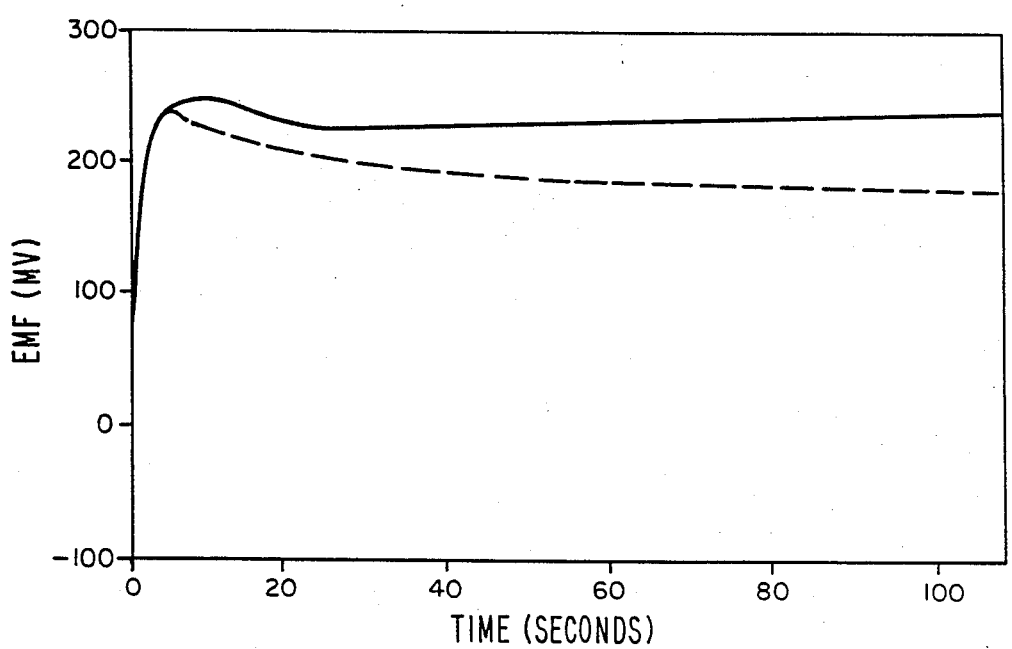

Oxygen sensors in accordance with the present invention have been shown to exhibit improved stability over previously available sensors. This is especially noteworthy during the measurement of low oxygen concentrations such as below about 10 ppm. FIGS. 6, 7 and 8 compare the performance of oxygen sensors of the invention (solid lines) employing chromium-chromium oxide reference electrodes, with cells from oxygen sensors (Celox ®) commerically available from the Electro-Nite Company.

FIG. 6 depicts the response at an oxygen concentration of 0.7 ppm while FIGS. 7 and 8 represent oxygen concentrations of 120 ppm and 650 ppm respectively. At the low oxygen concentration of FIG. 6, the commercial oxygen sensors are badly in error. The absolute values of the EMF measured by commercial oxygen sensors are always lower than that measured by the sensors of the present invention because of poor interfacial contact between sensing electrolyte and reference electrode material in prior sensors together with the high electronic conductivity associated with the magnesia-stabilized electrolyte of the commercial devices. It has been found that oxygen sensors in accordance with this invention can measure oxygen concentrations below 0.5 ppm. This is a vast improvement of the sensitivities available with prior materials and devices.

We claim:

1. An electrochemical sensor for a species comprising:

(a) a shaped body isostatically formed from a blend, said blend comprising a solid solution having a fluorite crystal structure comprising:
 a metal oxide; and
 admixed with said metal oxide, an oxide of an element from group IIA or IIIB of the periodic table in an amount sufficient to render said blend ionically conductive; and (b) an electrode in contact with said shaped body, said shaped body having not been subjected to sintering or thermal densification.

2. The sensor of claim 1 wherein the metal oxide comprises zirconia, thoria, hafnia or mixtures thereof.

3. The sensor of claim 2 wherein the admixed oxide comprises scandium, yttrium, calcium or magnesium oxide or mixtures thereof.

4. The sensor of claim 1 wherein the admixed oxide comprises scandium, yttrium, calcium or magnesium oxide or mixtures thereof.

5. The sensor of claim 1 wherein the blend consists of the solid solution.

6. The sensor of claim 1 further comprising admixing with said blend a carbon sensing amount of a carbide of the element of group IIA, IIIB, or IVB of the periodic table.

7. The sensor of claim 1 further comprising admixing with the blend a sulfur sensing amount of a sulfide of the element of group IIA, IIIB, or IVB of the periodic table.

8. The sensor of claim 1 wherein said electrode comprises a reference electrode composition in physical contact with said shaped body.

9. The sensor of claim 8 wherein said reference electrode composition comprises an isostatically compressed form.

10. The sensor of claim 8 wherein the reference electrode composition comprises a mixture of a metal and its oxide.

11. The sensor of claim 10 wherein said metal is either chromium or molybdenum.

12. The sensor of claim 1 wherein the blend has been isostatically compressed at a pressure of at least about 30,000 psi and subsequently comminuted prior to the isostatic formation of the shaped body.

13. The sensor of claim 12 wherein the isostatic formation of the shaped body is performed at a pressure of at least about 70,000 psi.

14. The sensor of claim 1 wherein the isostatic formation of the shaped body is performed at a pressure of at least about 70,000 psi.

15. The sensor of claim 1 wherein said shaped body comprises at least about 95% of a single solid phase.

16. The sensor of claim 1 wherein the density of the shaped body is less than about 90% of the theoretical density of the blend.

17. The sensor of claim 1 wherein said shaped body comprises at least about 80% of the theoretical density of the blend.

18. A method of fabricating an electrochemical sensor for a species comprising:

(a) selecting a metal oxide;
(b) admixing with said metal oxide, an oxide of an element from groups IIA or IIIB of the periodic table of the elements to form a blend in an amount sufficient to render said blend ionically conducting;
(c) isostatically forming said blend into a shaped body without simultaneous or subsequent sintering or thermal densification of said body; and (d) placing said shaped body in contact with an electrode.

19. The method of claim 18 wherein the metal oxide comprises zirconia, thoria, hafnia or mixtures thereof.

20. The method of claim 19 wherein the admixed oxide comprises scandium, yttrium, calcium or magnesium oxide or mixtures thereof.

21. The method of claim 18 wherein the admixed oxide comprises scandium, yttrium, calcium or magnesium oxide or mixtures thereof.

22. The method of claim 18 wherein the blend comprises a solid solution having a fluorite crystal structure.

23. The method of claim 18 further comprising admixture with said blend a carbon sensing amount of a carbide of the element of group IIA, IIIB, or IVB of the periodic table.

24. The method of claim 18 further comprising admixing with the blend a sulfur sensing amount of a sulfide of the element of group IIA, IIIB, or IVB of the periodic table.

25. The method of claim 18 wherein said electrode comprises a reference electrode composition.

26. The method of claim 25 further comprising isostatically compressing said reference electrode composition into a form.

27. The method of claim 25 wherein the reference electrode composition comprises a mixture of a metal and its oxide.

28. The method of claim 27 wherein said metal is either chromium or molybdenum.

29. The method of claim 18 further comprising isostatically compressing the blend at a pressure of at least about 30,000 psi and subsequently comminuting said blend prior to the isostatic formation of the shaped body.

30. The method of claim 29 wherein the isostatic formation of the shaped body is performed at a pressure of at least about 70,000 psi.

31. The method of claim 18 wherein the isostatic formation of the shaped body is performed at a pressure of at least about 70,000 psi.

32. The method of claim 18 wherein said shaped body comprises at least about 95% of a single solid phase.

33. The method of claim 18 wherein the density of the shaped body is less than about 90% of the theoretical density of the blend.

34. The method of claim 18 wherein the density of the shaped body is less than about 80% of the theoretical density of the blend.

35. A method of monitoring the concentration of a species in a metallurgical melt comprising contacting said melt with an electrochemical sensor prepared in accordance with the method of claim 18.

* * * * *